(12) United States Patent
Bel-Rhlid et al.

(10) Patent No.: US 10,526,621 B2
(45) Date of Patent: Jan. 7, 2020

(54) METHOD OF FORMING DIHYDROFERULIC ACID

(71) Applicant: NESTEC S.A., Vevey (CH)

(72) Inventors: Rachid Bel-Rhlid, Savigny (CH); Kaori Minehira Castelli, Corsier-sur-Vevey (CH); Stephane Duboux, St-Prex (CH); Laure Poquet, Servion (CH)

(73) Assignee: Soceite des Produits Nestle S.A., Vevey (CH)

( * ) Notice: Subject to any disclaimer, the term of this patent is extended or adjusted under 35 U.S.C. 154(b) by 11 days.

(21) Appl. No.: 15/563,990

(22) PCT Filed: Mar. 24, 2016

(86) PCT No.: PCT/EP2016/056651
§ 371 (c)(1),
(2) Date: Oct. 3, 2017

(87) PCT Pub. No.: WO2016/162227
PCT Pub. Date: Oct. 13, 2016

(65) Prior Publication Data
US 2018/0135083 A1   May 17, 2018

(30) Foreign Application Priority Data
Apr. 9, 2015  (EP) ..................................... 15162916

(51) Int. Cl.
| | | |
|---|---|---|
| *C12P 7/42* | (2006.01) | |
| *A61K 31/192* | (2006.01) | |
| *A23L 33/135* | (2016.01) | |
| *A23K 10/18* | (2016.01) | |
| *A23K 20/111* | (2016.01) | |
| *A23L 7/10* | (2016.01) | |
| *A23L 7/104* | (2016.01) | |
| *A61P 3/00* | (2006.01) | |
| *A61P 9/00* | (2006.01) | |
| *A61P 3/10* | (2006.01) | |
| *A61P 9/12* | (2006.01) | |
| *A23C 9/123* | (2006.01) | |
| *A61K 35/747* | (2015.01) | |

(52) U.S. Cl.
CPC .............. *C12P 7/42* (2013.01); *A23C 9/1232* (2013.01); *A23K 10/18* (2016.05); *A23K 20/111* (2016.05); *A23L 7/104* (2016.08); *A23L 7/115* (2016.08); *A23L 33/135* (2016.08); *A61K 31/192* (2013.01); *A61K 35/747* (2013.01); *A61P 3/00* (2018.01); *A61P 3/10* (2018.01); *A61P 9/00* (2018.01); *A61P 9/12* (2018.01); *A23V 2002/00* (2013.01); *A23Y 2220/43* (2013.01)

(58) Field of Classification Search
None
See application file for complete search history.

(56) References Cited

U.S. PATENT DOCUMENTS

2011/0046235 A1*  2/2011  Bel-Rhlid ................. A23F 5/02
514/720

FOREIGN PATENT DOCUMENTS

| JP | 2014003929 | 1/2014 |
| WO | 2013190068 | 12/2013 |
| WO | 2014048888 | 4/2014 |

OTHER PUBLICATIONS

Srinivasan et al. "Ferulic Acid: Therapeutic Potential Through its Antioxidant Property" J. Clin. Biochem. Nutr., Mar. 2007, vol. 40, No. 2, pp. 92-100.
Hole et al. "Improved Bioavailability of Dietary Phenolic Acids in Whole Grain Barley and Oat Groat following Fermentation with Probiotic Lactobacillus acidophilus, Lactobacillus johnsonii, and Lactobacillus reuteri" Journal of Agricultural and Food Chemistry, 2012, vol, 60, pp. 6369-6375.
Knockaert et al. "Metabolism of ferulic acid during growth of Lactobacillus plantarum and Lactobacillus collinoides" J. Sci. Food Agric., 2012, vol. 92, pp. 2291-2296.
Ohmiya et al. "Anaerobic reduction of ferulic acid to dihydroferulic acid by Wolinella succinogenes from cow rumen" Applied Microbiology and Biotechnology, 1986, vol. 23, pp. 274-279.

* cited by examiner

*Primary Examiner* — Robert J Yamasaki
*Assistant Examiner* — Charles Zoltan Constantine
(74) *Attorney, Agent, or Firm* — K&L Gates LLP

(57) ABSTRACT

The present invention relates to a method of forming dihydroferulic acid comprising providing ferulic acid and incubating the ferulic acid with a bacterial preparation of *Lactobacillus johnsonii* CNCM 1-1225 or a bacterial preparation of natural derivatives of *Lactobacillus johnsonii* CNCM 1-1225. An aspect of the invention is a composition comprising dihydroferulic acid and a bacterial preparation of *Lactobacillus johnsonii* CNCM 1-1225 or its natural derivatives. A further aspect of the invention is a composition comprising ferulic acid and a bacterial preparation of *Lactobacillus johnsonii* CNCM 1-1225 or its natural derivatives for use in the treatment or prevention of metabolic disease. Further aspects of the invention are the use of a bacterial preparation of *Lactobacillus johnsonii* CNCM 1-1225 or its natural derivatives; and a kit for preparing a food product.

12 Claims, No Drawings

METHOD OF FORMING DIHYDROFERULIC ACID

CROSS REFERENCE TO RELATED APPLICATIONS

The present application is a National Stage of International Application No. PCT/EP2016/056651, filed on Mar. 24, 2016, which claims priority to European Patent Application No. 15162916.9, filed on Apr. 9, 2015, the entire contents of which are being incorporated herein by reference.

FIELD OF THE INVENTION

The present invention relates to a method of forming dihydroferulic acid comprising providing ferulic acid and incubating the ferulic acid with a bacterial preparation of *Lactobacillus johnsonii* CNCM I-1225 or a bacterial preparation of natural derivatives of *Lactobacillus johnsonii* CNCM I-1225. An aspect of the invention is a composition comprising dihydroferulic acid and a bacterial preparation of *Lactobacillus johnsonii* CNCM I-1225 or its natural derivatives. A further aspect of the invention is a composition comprising ferulic acid and a bacterial preparation of *Lactobacillus johnsonii* CNCM I-1225 or its natural derivatives for use in the treatment or prevention of metabolic disease. Further aspects of the invention are the use of a bacterial preparation of *Lactobacillus johnsonii* CNCM I-1225 or its natural derivatives; and a kit for preparing a food product.

BACKGROUND OF THE INVENTION

The current diabetes pandemic is a serious problem confronting the health care system. Dihydroferulic acid (DHFA) has been shown to have an anti-hyperglycaemic effect through inhibition of gluconeogenesis (WO2014/048888). The compound dihydroferulic acid is illustrated by Formula I below:

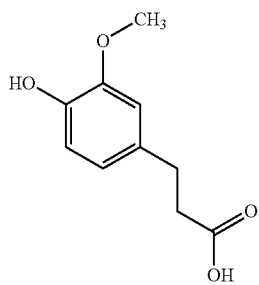

DHFA may be produced by enzymatic processing of wheat bran, but the speed, yield and selectivity of the reaction is not optimal. *Lactobacillus plantarum* has been shown to metabolise ferulic acid into a mixture of 4-vinylguaiacol and DHFA [Dries Knockaert et al., J. Sci. Food Agric., 92, 2291-2296. (2012)]. DHFA may also be chemically synthesised. However, it would be advantageous to provide a method of forming DHFA with good reaction speed, yield and selectivity, ideally using natural materials.

It would also be advantageous to be able to provide the beneficial effects of DHFA through a composition which is edible and is formed from materials coming from a natural source, especially materials which are already considered to have health benefits.

SUMMARY OF THE INVENTION

An object of the present invention is to improve the state of the art and to provide an improved method to overcome at least some of the inconveniences described above or at least to provide a useful alternative. The object of the present invention is achieved by the subject matter of the independent claims. The dependent claims further develop the idea of the present invention. Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

Accordingly, the present invention provides in a first aspect a method of forming dihydroferulic acid, the method comprising providing ferulic acid; and incubating the ferulic acid with a bacterial preparation of *Lactobacillus johnsonii* CNCM I-1225 or a bacterial preparation of natural derivatives of *Lactobacillus johnsonii* CNCM I-1225. In a second aspect, the invention relates to a composition comprising dihydroferulic acid and a bacterial preparation of *Lactobacillus johnsonii* CNCM I-1225 and/or a bacterial preparation of a natural derivative of *Lactobacillus johnsonii* CNCM I-1225. In a further aspect, the invention relates to a composition comprising ferulic acid and a bacterial preparation of *Lactobacillus johnsonii* CNCM I-1225 or a bacterial preparation of a natural derivative of *Lactobacillus johnsonii* CNCM I-1225 for use in the treatment of prevention of metabolic disease. A further aspect of the invention relates to the use of a bacterial preparation of *Lactobacillus johnsonii* CNCM I-1225 to convert ferulic acid to dihydroferulic acid. A still further aspect of the invention relates to a kit for preparing a food product, food supplement or beverage, containing at least two parts; a first part comprising a ferulic acid containing food ingredient; and a second part comprising a bacterial preparation of *Lactobacillus johnsonii* CNCM I-1225 or a bacterial preparation of a natural derivative of *Lactobacillus johnsonii* CNCM I-1225.

It has been surprisingly found by the inventors that *Lactobacillus johnsonii* CNCM I-1225 was able to convert ferulic acid into dihydroferulic acid from the pure ferulic acid as well as from hydrolyzed wheat bran rich in ferulic acid. Unexpectedly, *L. johnsonii* NCC 533 was more effective than *L. plantarum* strains. *L. plantarum* has previously been reported to convert ferulic acid into dihydroferulic acid [Knockaert et al., J. Sci. Food Agric., 92, 2291-2296 (2012)]. The inventors investigated whether other strains of *L. johnsonii* species were able to transform ferulic acid into dihydroferulic acid, and found that *Lactobacillus johnsonii* CNCM I-1225 has an unusual potency for performing this conversion at high yields. The inventors were surprised to find that *Lactobacillus johnsonii* CNCM I-1225 was able to perform this conversion in hydrolyzed wheat bran as, under the same conditions, neither the *Lactobacillus johnsonii* type strain nor *Lactobacillus sp.* JCM 2010 were able to convert ferulic acid into dihydroferulic acid.

The inventors found that *Lactobacillus johnsonii* CNCM I-1225 was able to convert ferulic acid in hydrolyzed wheat bran into dihydroferulic acid at higher yields than *Lactobacillus johnsonii* JCM 2122, which had been described in JP2014003929 as demonstrating activity for reducing ferulic acid in plants to dihydroferulic acid. As *Lactobacillus johnsonii* CNCM I-1225 is a known probiotic, with a successful history of human consumption in commercial products, it is advantageous that this strain of *Lactobacillus johnsonii* may be used to form dihydroferulic acid.

DETAILED DESCRIPTION OF THE INVENTION

Consequently the present invention relates in part to a method of forming dihydroferulic acid, the method comprising providing ferulic acid and incubating the ferulic acid with a bacterial preparation of *Lactobacillus johnsonii* CNCM I-1225 (NCC 533) or a bacterial preparation of natural derivatives of *Lactobacillus johnsonii* CNCM I-1225.

*Lactobacillus johnsonii* NCC 533 (also named La1) was deposited with the Collection Nationale de Cultures de Microorganismes (CNCM), Institut Pasteur, 25 rue du Docteur Roux, F-75724 PARIS Cedex 15, France, on 30 Jun. 1992 and given the deposit number 1-1225.

Ferulic acid, or (E)-3-(4-hydroxy-3-methoxy-phenyl) prop-2-enoic acid is a hydroxycinnamic acid found in the seeds of coffee, apple, artichoke, peanut, and orange, as well as in both seeds and cell walls of plants such as rice, wheat and oats. Ferulic acid exhibits a wide range of therapeutic effects against various diseases like cancer, diabetes, cardiovascular disease and neurodegenerative disease [Marimuthu Srinivasan et. Al., J. Clin. Biochem. Nutr., 40(2): 92-100 (2007).]

Natural derivatives of *Lactobacillus johnsonii* CNCM I-1225 are viable and genetically stable variants of *Lactobacillus johnsonii* CNCM I-1225. Changes in the genome sequence occur naturally, e.g. due to mis-repair of damaged DNA, or errors in DNA replication, with relatively low frequency. Variants may be identified by screening. WO2012/130965 describes natural D-lactic acid variants of *Lactobacillus johnsonii* CNCM I-1225. The natural derivatives of *Lactobacillus johnsonii* CNCM I-1225 may be deficient in D-lactic acid production. For example, the natural derivatives of *Lactobacillus johnsonii* CNCM I-1225 may be selected from the group consisting of *Lactobacillus johnsonii* CNCM I-4432, *Lactobacillus johnsonii* CNCM I-4433, *Lactobacillus johnsonii* CNCM I-4438, *Lactobacillus johnsonii* CNCM I-4439, *Lactobacillus johnsonii* CNCM I-4440, *Lactobacillus johnsonii* CNCM I-4442, *Lactobacillus johnsonii* CNCM I-4443 and combinations of these.

*Lactobacillus johnsonii* CNCM I-4432, *Lactobacillus johnsonii* CNCM I-4433, *Lactobacillus johnsonii* CNCM I-4438, *Lactobacillus johnsonii* CNCM I-4439, *Lactobacillus johnsonii* CNCM I-4440, *Lactobacillus johnsonii* CNCM I-4442 and *Lactobacillus johnsonii* CNCM I-4443 were deposited on Feb. 8, 2011, with the Collection Nationale de Cultures de Microorganismes (CNCM), Institut Pasteur, 25 Rue du Docteur Roux, F-75724 Paris Cedex 15, France, under the Budapest Treaty.

The bacterial preparation of the present invention is not particularly limited in form. It may be an aqueous suspension of bacteria; a paste; or a powder, for example lyophilized bacteria which may include lyoprotective media. The bacterial preparation may be a starter culture, for example a cultivation medium which has been well colonized by microorganisms. The bacterial preparation may be a cell culture which has been subjected to lysis. Incubating the ferulic acid with the bacterial preparation may include the addition of water to the bacterial preparation. Preferably the ferulic acid is incubated in a liquid which contains between $10^5$ and $10^{11}$ colony forming units per ml of *Lactobacillus johnsonii* CNCM I-1225 or natural derivatives of *Lactobacillus johnsonii* CNCM I-1225. The bacterial preparation may comprise cells in their growing phase (fermentation) or in their stationary phase (resting cells). For example, resting cells may be obtained by centrifuging a culture of *Lactobacillus johnsonii* CNCM I-1225 (or natural derivatives of *Lactobacillus johnsonii* CNCM I-1225). The resting cells will be in the pellet after centrifugation and may be added to ferulic acid to incubate it.

The bacterial preparation of the present invention may comprise a fermentation broth or extract of a fermentation broth of *Lactobacillus johnsonii* CNCM I-1225 or natural derivatives of *Lactobacillus johnsonii* CNCM I-1225. The term fermentation broth refers to the culture medium resulting after fermentation of a microorganism and encompasses the microorganism and its component parts, unused raw substrates, and metabolites produced by the microorganism during fermentation, among other things. The fermentation broth may be a concentrated fermentation broth.

The bacterial preparation may be obtained as a by-product from the production of bacteria. Often, once the bacterial cells have been removed or "harvested" from a fermentation broth, the rest of the broth is discarded. This is wasteful and it is often costly to ensure a safe and environmentally responsible disposal of the remaining broth. It is therefore an advantage that this by-product can be beneficially used in the current invention.

The *Lactobacillus johnsonii* CNCM I-1225 or natural derivatives of *Lactobacillus johnsonii* CNCM I-1225 may have been at least partially removed from the fermentation broth in the method of the invention. Preferably the fermentation broth before the at least partial removal of the lactic acid bacteria contains between $10^5$ and $10^{11}$ colony forming units (CFU) per ml. In the present invention, "at least partially removed" means that at least 50% of the viable *Lactobacillus johnsonii* bacteria present in the bacterial preparation have been removed, for example at least 80% of the viable *Lactobacillus johnsonii* bacteria have been removed. Examples of a bacterial preparation wherein the lactic acid bacteria have been at least partially removed may be a culture filtrate, or the supernatant of a culture after centrifugation. Such filtrates or supernatants may be concentrated or fractionated.

The ferulic acid in the method of the invention may be obtained by the hydrolysis of natural materials, for example lignocellulosic biomass. Lignocellulosic biomass can for example be wood, agricultural residues, water plants and grasses. The ferulic acid in the method of the invention may be obtained by the hydrolysis of bran, for example wheat bran. The bran may be comprised within a whole grain. Whole grains are cereal grains that contain the germ, endosperm, and bran. The whole grain may be a ground whole grain. Bran is a popular food ingredient with good consumer acceptability and nutritional value. It is particularly rich in dietary fibre and essential fatty acids and contains significant quantities of starch, protein, vitamins and dietary minerals. The hydrolysis of the bran to obtain ferulic acid may be performed by enzymes, for example a commercial mixture of xylanase and feruloyl esterase. An aspect of the invention is a composition obtained, for example obtainable, by the method of the invention.

In another aspect, the invention provides a composition comprising dihydroferulic acid (for example at a level of at least 0.01 wt. % in the composition) and a bacterial preparation of *Lactobacillus johnsonii* CNCM I-1225 or a bacterial preparation of a natural derivative of *Lactobacillus johnsonii* CNCM I-1225. This can provide the dual benefits of glucose management and probiotic health benefits such as immunomodulation or pathogen inhibition. Gut microbiota metabolites such as dihydroferulic acid can favourably control blood glucose. The composition comprising dihydroferulic acid and a bacterial preparation of *Lactobacillus johnsonii* CNCM I-1225 or a bacterial preparation of a natural derivative of *Lactobacillus johnsonii* CNCM I-1225 may be for use in the treatment or prevention of metabolic disease. The composition may comprise at least $10^5$ CFU per ml of *Lactobacillus johnsonii* CNCM I-1225 or a natural derivative of *Lactobacillus johnsonii* CNCM I-1225. For example the composition may comprise between $10^5$ and $10^{12}$ CFU per ml of *Lactobacillus johnsonii* CNCM I-1225 or a natural derivative of *Lactobacillus johnsonii* CNCM I-1225. The composition may comprise between $10^5$ and $10^{12}$ CFU per ml of *Lactobacillus johnsonii* CNCM I-1225 or a natural derivative of *Lactobacillus johnsonii* CNCM I-1225 and between 20 and 500 mg dihydroferulic acid. The dihydroferulic acid may be from a natural source, for example the dihydroferulic acid may be from a natural source of ferulic acid (such as hydrolyzed bran) which has been converted to dihydroferulic acid by the action of *Lactobacillus johnsonii* CNCM I-1225 or a natural derivative of *Lactobacillus johnsonii* CNCM I-1225.

The composition may further comprise hydrolyzed bran, for example hydrolyzed wheat bran. For example the composition may comprise bran hydrolyzed by a combination of carbohydrase (such as xylanase) and feruloyl esterase, the combination of carbohydrase and feruloyl esterase being for example a mixture of carbohydrase and feruloyl esterase or the sequential application of carbohydrase and feruloyl esterase. It is advantageous to be able to provide dihydroferulic acid formed from materials coming from a natural source, especially when combined with other components with beneficial effects such as *Lactobacillus johnsonii* CNCM I-1225 which has well documented health benefits such as immunomodulation and pathogen inhibition. The composition may also comprise ferulic acid, for example in a composition where ferulic acid has been incubated with a bacterial preparation of *Lactobacillus johnsonii* CNCM I-1225 or natural derivatives of *Lactobacillus johnsonii* CNCM I-1225, but has only partially been converted to dihydroferulic acid.

The bacterial preparation comprised within the composition of the invention may be a fermentation broth or extract of a fermentation broth of *Lactobacillus johnsonii* CNCM I-1225 or natural derivatives of *Lactobacillus johnsonii* CNCM I-1225. The composition according to the invention may have been spray dried. The composition of the invention may form part of a food product, for example a beverage, dairy product, petfood, or food supplement.

In a further aspect the invention provides a composition comprising ferulic acid and a bacterial preparation of *Lactobacillus johnsonii* CNCM I-1225 or a bacterial preparation of a natural derivative of *Lactobacillus johnsonii* CNCM I-1225 for use in the treatment or prevention of metabolic disease. Gut microbiota metabolites such as dihydroferulic acid can favourably control blood glucose. By providing a composition having both ferulic acid and a bacterial preparation of *Lactobacillus johnsonii* CNCM I-1225 or a bacterial preparation of a natural derivative of *Lactobacillus johnsonii* CNCM I-1225 the production of dihydroferulic acid in the gut is greatly enhanced. The composition for use according to the invention may further comprise dihydroferulic acid, for example the composition may be a fermentation broth (for example a concentrated fermentation broth) of *Lactobacillus johnsonii* CNCM I-1225 or *Lactobacillus johnsonii* CNCM I-1225 in which ferulic acid has been incubated to convert part of the ferulic acid to dihydroferulic acid.

The composition comprising ferulic acid and a bacterial preparation of *Lactobacillus johnsonii* CNCM I-1225 or a bacterial preparation of a natural derivative of *Lactobacillus johnsonii* CNCM I-1225 for use in the treatment or prevention of metabolic disease may be administered in a daily dose to provide between 1 and 8 mg/kg body weight of ferulic acid, and between $10^5$ and $10^{11}$ CFU per kg body weight of *Lactobacillus johnsonii* CNCM I-1225 or a natural derivative of *Lactobacillus johnsonii* CNCM I-1225, for example between 2 and 5 mg/kg body weight of ferulic acid, and between $10^7$ and $10^9$ CFU per kg body weight of *Lactobacillus johnsonii* CNCM I-1225 or a natural derivative of *Lactobacillus johnsonii* CNCM I-1225.

The composition for use according to the present invention is to be provided to a subject. In an embodiment, the subject is a mammal, such as a human, a cat, a dog or a horse.

The composition comprising ferulic acid and a bacterial preparation of *Lactobacillus johnsonii* CNCM I-1225 or a bacterial preparation of a natural derivative of *Lactobacillus johnsonii* CNCM I-1225 for use in the treatment or prevention of diabetes, hyperlipidemia, hypertension or cardiovascular disease. Diabetes, hyperlipidemia, hypertension and cardiovascular disease are metabolic diseases.

The ferulic acid comprised within the composition for use according to the invention may be from a natural source. The ferulic acid in the composition for use according to the invention may be comprised within hydrolyzed bran, for example within hydrolyzed whole meal. The ferulic acid in the composition for use according to the invention may be obtained by the hydrolysis of bran using a combination of a carbohydrase (such as xylanase) and feruloyl esterase. The ferulic acid in the composition for use according to the invention may be comprised within hydrolyzed wheat bran.

The bacterial preparation comprised within the composition for use according to the invention may be a fermentation broth or extract of a fermentation broth of *Lactobacillus johnsonii* CNCM I-1225 or natural derivatives of *Lactobacillus johnsonii* CNCM I-1225.

The composition for use according to the invention may have been spray dried. The composition for use according to the invention may be combined with an excipient. For example, the composition for use according to the invention may be combined with an excipient and formed into a pressed tablet or filled into a capsule.

The composition for use according to the invention may form part of a food product. Thus, in one aspect the invention relates to a food product comprising the composition for use according to the invention. In yet an aspect the invention relates to a composite food product, wherein at least one part of the composite food products comprises the composition for use according to the invention. This may be the case where a food product is constituted of multiple independent parts (composite), where e.g. only one of the parts comprises the composition for use according to the invention.

The food product, of which the composition for use according to the invention may form part, may be selected from the group consisting of beverages, dairy products, petfood, and food supplements. Examples of beverages according to the present invention are meal replacements, oral nutritional supplements or ready-to-drink beverages supplemented with hydrolyzed whole grain. The dairy products according to the present invention may be powdered milk products, for example a powdered milk product comprising milk powder, ferulic acid, spray dried *Lactobacillus johnsonii* CNCM I-1225 and optionally vitamins and minerals. The dairy products according to the present invention may be fermented milk products such as yoghurts. In the context of the present invention the term yoghurt may include, but is not limited to, materials complying with local food labelling regulations concerning the term "yoghurt". Examples of petfood according to the present invention may be selected from the group consisting of kibbles and pellets. A food supplement, also known as a nutritional supplement or dietary supplement, is a preparation intended to supplement the diet and provide nutrients, such as vitamins, minerals, fibre, fatty acids, or amino acids that may be missing or may not be consumed in sufficient quantities in a person's diet. Examples of the form of food supplements according to the present invention are capsules and pills.

In a further aspect, the invention provides the use of a bacterial preparation of *Lactobacillus johnsonii* CNCM I-1225 or a bacterial preparation of a natural derivative of *Lactobacillus johnsonii* CNCM I-1225 to convert ferulic acid to dihydroferulic acid.

In a still further aspect, the invention provides a kit for preparing a food product containing at least two parts; a first part comprising a ferulic acid containing food ingredient; and a second part comprising a bacterial preparation of *Lactobacillus johnsonii* CNCM I-1225 or a bacterial preparation of a natural derivative of *Lactobacillus johnsonii* CNCM I-1225. The ferulic acid containing food may comprise hydrolyzed bran, for example hydrolyzed whole grain.

Those skilled in the art will understand that they can freely combine all features of the present invention disclosed herein. In particular, features described for the compositions of the present invention may be combined with the method of the present invention and vice versa. Further, features described for different embodiments of the present invention may be combined. Where known equivalents exist to specific features, such equivalents are incorporated as if specifically referred to in this specification. Further advantages and features of the present invention are apparent from the non-limiting examples.

EXAMPLES

Example 1: Bioconversion in Growth Medium

Different bacterial strains were compared to test their ability to convert ferulic acid (FA) into dihydroferulic acid (DHFA).

*Lactobacillus plantarum* ATCC® 14917™ is the *Lactobacillus plantarum* type strain, available from American Type Culture Collection, Manassas, USA. Its reference numbers in other collections include LMG 6907, used in the study by Knockaert [Dries Knockaert et al., J. Sci. Food Agric., 92, 2291-2296. (2012)].

*Lactobacillus paracasei* NCC 2461 was deposited with the Collection Nationale de Cultures de Microorganismes (CNCM), Institut Pasteur, 25 rue du Docteur Roux, F-75724 PARIS Cedex 15, France, on 12 Jan. 1999 and given the deposit number 1-2116.

*Bifidobacterium lactis* NCC 2818 was deposited with the Collection Nationale de Cultures de Microorganismes (CNCM), Institut Pasteur, 25 rue du Docteur Roux, F-75724 PARIS Cedex 15, France, on 7 Jun. 2005 and given the deposit number CNCM I-3446.

*Bifidobacterium longum* NCC 3001 was deposited by Morinaga, at the American Type Culture Collection (ATCC), under accession number ATCC BAA-999. It is publicly available, as shown for instance by the abstract PG3-11 by Mercenier et al., [J. Pediatr. Gastroenterol. Nutr. 3 May 2006; 43(5):E38.]

*Lactobacillus rhamnosus* NCC 4007 was deposited with the China General Microbiological Culture Collection Centre (CGMCC), Chinese Academy of Sciences, PO Box 2714, Beijing 100080, P.R. China, in October 2004 and given the deposit number 1,3724.

Strains were reactivated in two subsequent growths (o/n, anaerobiosis, 37° C.) in 10 ml MRS freshly supplemented with 0.05% cystein (MRS-Cys). MRS-Cys medium (10 ml) was supplemented with sterile filtered FA at a concentration of 3 mM and then inoculated at 2% from the re-activated culture and grown at 37° C. under anaerobic conditions. After 16 h, the cultures were centrifuged and the supernatants filtered through a 0.22 µm syringe filter and analyzed by Ultra-Performance Liquid Chromatography (UPLC).

FA and DHFA were separated using a C18-column Acquity UPLC BEH C18 1.8 µm, 2.1 mm×150 mm (Waters AG, Baden-Dättwil, Switzerland). The system consisted of an UPLC-PDA system, equipped with binary gradient pump and a Photodiode Array detector (PDA) (Waters AG, Baden-Dattwil, Switzerland). Samples were kept at 10° C. during the analysis and the chromatography was done at 40° C. Elution was performed with a flow rate set at 0.5 ml/min and a gradient of solvent A (water) and B (acetonitrile), both acidified with 1% acetic acid. UPLC analysis was started with 3% of solvent B. This condition was maintained for 1.8 min and then the percentage of solvent B was linearly increased to 15% within 5.4 min, to 21% within 2.7 min and finally to 90% within 0.1 min; 90% solvent B was maintained for 2 min, then initial conditions were reached within 0.1 min and the column equilibrated in 3% solvent B for 3.9 min. The detection was monitored with the PDA set at 280 nm.

As shown in table 1 below, other bacteria were able to completely metabolize FA, however, the maximum yield (100%) of DHFA production was reached only with *Lactobacillus johnsonii* CNCM I-1225. Some strains were able to transform FA, but not exclusively to DHFA. It is expected (but not measured) that these strains converted at least some of the FA into other metabolites.

TABLE 1

| Strain | DHFA (mM) | FA (mM) | % conversion of FA into DHFA |
|---|---|---|---|
| *Lactobacillus johnsonii* CNCM I-1225 | 3.12 | 0.00 | 100 |
| *Lactobacillus plantarum* ATCC 14917 | 1.62 | 0.00 | 54 |
| *Lactobacillus plantarum* CNCM I-4636 | 1.91 | 0.00 | 64 |
| *Lactobacillus paracasei* CNCM I-2116 | 0.0 | 2.75 | 0 |
| *Bifidobacterium lactis* CNCM I-3446 | 0.0 | 2.99 | 0 |
| *Bifidobacterium longum* ATCC BAA-999 | 0.0 | 2.88 | 0 |
| *Lactobacillus rhamnosus* CGMCC 1,3724 | 0.0 | 2.74 | 0 |

*Lactobacillus johnsonii* CNCM I-1225 is more effective than other strains at converting ferulic acid to dihydroferulic acid, including the type strain of *Lactobacillus plantarum* which has previously been shown to metabolise ferulic acid into DHFA [Knockaert (2012)].

Example 2: Bioconversion of Ferulic Acid from Hydrolyzed Wheat Bran with *L. johnsonii* Growing Cells Wheat bran (Minoteries, Granges-Marnand, Switzerland) was suspended in water (20% w/v) at 50° C. This solution was then heated for 10 min at 90° C. Pentopan 500 GB (Novozymes) was then added to the solution of wheat bran at 65° C. and a concentration of 0.5% w/w. After 2 h reaction time, the solution was heated for 10 min at 90° C. This treatment resulted in the release of 2.56 mg/g of ferulic acid. No free FA or DHFA were identified in the non-treated wheat bran.

A solution of hydrolyzed wheat bran (10% w/v) in 750 ml sterile water and incubated in a DasGip fermenter for 16 hours with 3 different bacterial strains. All strains grew well on the hydrolyzed wheat bran. Table 2 below shows the colony forming units counts before and after fermentation of the hydrolyzed wheat bran. FA and DHFA were measured by UPLC. 2.56 mg/g FA was present before fermentation, DHFA was not present before fermentation.

TABLE 2

| Strain | CFU/ml at inoculation | CFU/ml after 16 h of fermentation |
| --- | --- | --- |
| *Lactobacillus johnsonii* CNCM I-1225 | 1.15E+07 | 6.00E+08 |
| *Lactobacillus johnsonii* ATCC 33200 | 3.45E+07 | 1.58E+09 |
| *Lactobacillus plantarum* ATCC 14917 | 3.40E+07 | 1.18E+09 |

*Lactobacillus johnsonii* ATCC® 33200™ is the *Lactobacillus johnsonii* type strain, available from American Type Culture Collection, Manassas, USA.

Out of the 3 tested bacteria strains, only *Lactobacillus johnsonii* CNCM I-1225 was able to convert 100% of the FA into DHFA. *Lactobacillus plantarum* ATCC 14917 which had converted FA to DHFA in the MRS medium supplemented with FA (Example 1) did not show this activity on the hydrolyzed wheat bran. No added sugars such as dextrose were required for the growth of *Lactobacillus johnsonii* CNCM I-1225 on hydrolyzed wheat bran. Table 3 shows the bioconversion of hydrolyzed wheat bran using different strains.

TABLE 3

| Strain | DHFA (mg/g dry matter) | FA (mg/g dry matter) | % conversion of FA into DHFA |
| --- | --- | --- | --- |
| *Lactobacillus johnsonii* CNCM I-1225 | 2.63 | 0.0 | 100 |
| *Lactobacillus johnsonii* ATCC 33200 | 0.0 | 2.33 | 0 |
| *Lactobacillus plantarum* ATCC 14917 | 0.0 | 1.93 | 0 |

This demonstrates that incubating ferulic acid in the form of hydrolyzed wheat bran with a bacterial preparation of *L. johnsonii* CNCM I-1225 leads to the conversion of ferulic acid to dihydroferulic acid at high yields.

Example 3: Bioconversion of Ferulic Acid *L. johnsonii* Resting Cells

An overnight culture of *L. johnsonii* CNCM I-1225 in MRS (150 ml, 37° C., aerobic) was centrifuged at 3300 g for 20 min. The supernatant was discarded and the pellet suspended in 3 ml of PBS and added to a solution of hydrolyzed wheat bran (10% w/v) in 750 ml sterile water and incubated in a DasGip fermenter for 4 h and 16 h. FA and DHFA were analyzed by UPLC. Results with stationary phase cells are shown in Table 4:

| Sample | DHFA (mg/g dry matter) | FA (mg/g dry matter) |
| --- | --- | --- |
| Hydrolyzed wheat bran | 0 | 2.56 |
| 4 h incubation with *L. johnsonii* CNCM I-1225 | 1.61 | 1.05 |
| 16 h incubation with *L. johnsonii* CNCM I-1225 | 2.01 | 0.61 |

This demonstrates that incubating ferulic acid with a bacterial preparation of *L. johnsonii* CNCM I-1225 in the form of resting cells leads to the conversion of FA to DHFA, but with a lower conversion yield (76%) after 16 hours than when using growing cells (100%).

Example 4: Bioconversion of Ferulic Acid from Hydrolyzed Wheat Bran with Different *L. johnsonii* Growing Cells Wheat bran (Minoteries, Granges-Marnand, Switzerland) was suspended in water (20% w/v) at 50° C. This solution was then heated for 10 min at 90° C. Pentopan 500 GB (Novozymes) was then added to the solution of wheat bran at 65° C. and a concentration of 0.5% w/w. After 2 h reaction time, the solution was heated for 10 min at 90° C. and further dried by freeze-drying. This treatment resulted in the release of 2.56 mg/g of ferulic acid. No free FA or DHFA were identified in the non-treated wheat bran.

The dried hydrolyzed wheat bran was dissolved (15% w/v) in 100 ml sterile water and incubated and stirred in an Erlenmeyer for 16 hours at 37° C. with 4 different bacterial strains. All strains grew well on the hydrolyzed wheat bran. Table 5 below shows the pH values before and after fermentation of the hydrolyzed wheat bran. FA and DHFA were measured by UPLC. FA was present before fermentation, DHFA was not present before fermentation.

TABLE 5

| Strain | pH at inoculation | pH after 16 h of fermentation |
| --- | --- | --- |
| *Lactobacillus johnsonii* CNCM I-1225 | 5.98 | 4.04 |
| *Lactobacillus johnsonii* ATCC 33200 | 5.98 | 4.18 |
| *Lactobacillus johnsonii* JCM 2122 | 5.98 | 4.08 |
| *Lactobacillus* sp. JCM 2010 | 5.98 | 4.66 |

*Lactobacillus johnsonii* ATCC® 33200™, *Lactobacillus johnsonii* JCM 2122 and *Lactobacillus* sp. JCM 2010 are publicly available. *Lactobacillus johnsonii* ATCC® 33200™ is the *Lactobacillus johnsonii* type strain, available from American Type Culture Collection, Manassas, USA, while *Lactobacillus johnsonii* JCM 2122 and *Lactobacillus* sp. JCM 2010 were obtained from the Japan Collection of Microorganisms (JCM) RIKEN Bioresource Center (RIKEN BRC), Japan.

Out of the 4 tested bacteria strains *Lactobacillus johnsonii* CNCM I-1225 showed the best conversion of FA into DHFA. *Lactobacillus johnsonii* JCM 2122 showed a lower level of conversion, while both *Lactobacillus johnsonii* ATCC 33200 and *Lactobacillus* sp. JCM 2010 showed no conversion of FA to DHFA. Table 6 shows the bioconversion of hydrolyzed wheat bran using different strains.

TABLE 6

| Strain | DHFA (mg/g dry matter) | FA (mg/g dry matter) | % conversion of FA into DHFA |
|---|---|---|---|
| *Lactobacillus johnsonii* CNCM I-1225 | 1.21 | 1.14 | 51.5 |
| *Lactobacillus johnsonii* ATCC 33200 | 0.0 | 2.23 | 0.0 |
| *Lactobacillus johnsonii* JCM 2122 | 0.58 | 1.68 | 25.6 |
| *Lactobacillus* sp. JCM 2010 | 0.0 | 2.31 | 0.0 |

This demonstrates that incubating ferulic acid in the form of hydrolyzed wheat bran with a bacterial preparation of *L. johnsonii* CNCM I-1225 leads to the conversion of ferulic acid to dihydroferulic acid at high yields as compared to other strains.

The invention claimed is:

1. A method of forming dihydroferulic acid, the method comprising providing at least one material selected from the group consisting of pure ferulic acid and hydrolyzed wheat bran; and incubating the at least one material with a bacterial preparation comprising at least one of *Lactobacillus johnsonii* CNCM I-1225 or a natural derivative thereof that is selected from the group consisting of *L. johnsonii* CNCM I-4432, *L. johnsonii* CNCM I-4433, *L. johnsonii* CNCM I-4438, *L. johnsonii* CNCM I-4439, *L. johnsonii* CNCM I-4440, *L. johnsonii* CNCM I-4442, *L. johnsonii* CNCM I-4443 and combinations thereof, under conditions sufficient to produce dihydroferulic acid.

2. The method according to claim 1 wherein the bacterial preparation comprises a fermentation broth or extract of a fermentation broth of the at least one of *Lactobacillus johnsonii* CNCM I-1225 or natural derivative thereof.

3. The method according to claim 2 wherein the at least one of *Lactobacillus johnsonii* CNCM I-1225 or natural derivative thereof has been at least partially removed from the fermentation broth.

4. The method according to claim 1 wherein the at least one material is hydrolyzed wheat bran.

5. The method according to claim 4 wherein the hydrolyzed wheat bran comprises ferulic acid.

6. The method according to claim 5 wherein the bioconversion to the dihydroferulic acid is about 100% of the ferulic acid in the hydrolyzed wheat bran.

7. The method according to claim 1 wherein the at least one of *Lactobacillus johnsonii* CNCM I-1225 or natural derivative thereof is in a form of resting cells.

8. The method according to claim 1 wherein the at least one of *Lactobacillus johnsonii* CNCM I-1225 or natural derivative thereof is in a form of growing cells.

9. The method according to claim 1 wherein the incubating of the at least one material with the bacterial preparation is performed at about 37° C. for up to about 16 hours under an anaerobic condition.

10. The method according to claim 1 wherein no detectable amount of free ferulic acid is present after the incubating of the at least one material with the bacterial preparation.

11. The method according to claim 1 wherein the at least one material is pure ferulic acid.

12. The method according to claim 11 wherein the bioconversion to the dihydroferulic acid is about 100% of the pure ferulic acid.

* * * * *